United States Patent [19]

Rieber et al.

[11] 4,235,794

[45] Nov. 25, 1980

[54] METHOD FOR THE MANUFACTURE OF METAL SOAP GRANULATES

[75] Inventors: Gernot Rieber, Munich; Thomas H. Miller, Gauting, both of Fed. Rep. of Germany

[73] Assignee: Chemische Werke Munchen Otto Barlocher GmbH, Munich, Fed. Rep. of Germany

[21] Appl. No.: 38,797

[22] Filed: May 14, 1979

[30] Foreign Application Priority Data

May 26, 1978 [DE] Fed. Rep. of Germany ....... 2823002

[51] Int. Cl.³ .......................... C11C 1/00; C09K 15/32
[52] U.S. Cl. ..................................... 260/413; 260/414;
106/308 F; 252/8.1; 252/17; 252/32; 252/134; 252/400 R
[58] Field of Search ........................... 260/413 S, 414; 252/134

[56] References Cited

U.S. PATENT DOCUMENTS

| | | | |
|---|---|---|---|
| 2,809,121 | 11/1957 | Davis et al. | 260/414 |
| 3,168,540 | 2/1965 | Culemeyer | 260/414 |
| 3,773,664 | 11/1973 | Lesuer | 260/414 |
| 3,803,188 | 4/1974 | Scott | 260/413 S |
| 3,926,829 | 12/1975 | Smith et al. | 252/134 |
| 4,060,535 | 11/1977 | Cinco | 260/413 S |

*Primary Examiner*—John F. Niebling
*Attorney, Agent, or Firm*—Scully, Scott, Murphy & Presser

[57] ABSTRACT

This invention pertains to a process for the manufacture of metal soap granulates or mixtures thereof by means of reacting an aqueous solution or suspension of a metal oxide, metal hydroxide or metal carbonate, including basic metal carbonates, or mixtures thereof with a water insoluble fatty acid which may be aliphatic, saturated or unsaturated, straight chained or branched and which may either be natural or synthetic fatty acids, having a chain length of $C_8$–$C_{32}$ and a melting point of above 0° C. and below 100° C.; such fatty acids may be used alone or in mixtures with the reaction taking place in the absence of catalysts and wetting agents.

23 Claims, 1 Drawing Figure

METHOD FOR THE MANUFACTURE OF METAL SOAP GRANULATES

BACKGROUND OF THE INVENTION

Metal soaps are finding widespread use in the plastics industry especially in the processing of thermoplastics such as polyvinylchloride, polyethylene, polypropylene, polystyrene, ABS resins and others in the form of stabilizers, lubricants and release agents. These metal soaps are used in granular form since this enhances their ease of handling and processing.

It is known to produce metal soaps by means of a dual reaction. In this process the metal soaps are formed by precipitation from aqueous solutions of the alkali or ammonium salt of fatty acids caused by the addition of aqueous solutions of metal salts. Another widely used method is the neutralization reaction. According to German Pat. No. 8 60 210 this process employs an emulsion of the liquid fatty acid containing ammonia, alkylol amine or other useful nitrogen bases which is reacted with an aqueous suspension of metal oxides or metal hydroxides. Another process, especially for the manufacture of lead soaps is described in the German Auslegeschrift 10 68 238. According to this method, electrolyte-free normal lead salt of fatty acids having from 8 to 30 carbon atoms is obtained by mixing an aqueous suspension of lead oxide, whose temperature lies below the melting point of the fatty acid, with either molten, colloidial, flakes or pulverized fatty acid; such reaction taking place in the absence of catalysts or wetting agents. The metal soaps obtained by the above mentioned process constitute extremely fine, light and voluminous powders which are very prone to forming fine dusts. This means that their production and handling is subject especially to the constant danger of dust explosions as well as to health hazards arising from the toxic metal soap dust. This situation jeopardizes the use of these generally, essential, metal soaps, since very expensive protective measures have to be utilized. Another considerable disadvantage of metal soaps in powder form is found in their unsatisfactory flow characteristics. This does not permit their being handled in bulk which would otherwise allow for their economic transport and storage, as well as their use in automated proportioning equipment.

Many efforts have been made to produce dust-free metal soaps. However, none of the known processes described hereinafter for the production of metal soaps have attained technical importance. Thus it is known, according to the German Pat. No. 15 68 283, that granular mixed soaps can be produced from water insoluble acids and two or more bivalent metals. In this process a molten mixture of an organic, water insoluble acid and one of its dibasic metal salts is used. This liquid mixture is combined dropwise with an aqueous preparation containing an oxide or hydroxide of at least one additional bivalent metal which forms a salt of high melting point with the molten, water insoluble fatty acid. This process is restricted to the manufacture of specific metal soap combinations. Furthermore, the metal soaps thus produced proved generally unsatisfactory with regard to their practical application.

German Auslegeschrift 12 79 658 describes a method for the granulation of powdery masses, such as metal soaps, which is carried out in the aqueous phase with the use of difficult to dissolve or insoluble organic granulating aids at temperatures above 60° C. German Auslegeschrift 15 42 058 describes a method for the granulating of production aids, including metal soaps, used as additives for the plastics industry. In this process the powders which are to be granulated are combined with a binding agent having a hydrocarbon radical and the mass is then heated to above the melting point of the binding agent, during which time the mass is vigorously agitated. This is followed by less intense agitation while the reaction product cools. These processes used binding agents e.g. granulating aids, which limit the general applicability of such granulates considerably, since the nature of such agglutinants often causes increased material costs.

Long established methods for the production of dust-free products are tableting, extruding, flaking and spraying. These shaping or compacting processes, which are carried out in the sinter or melting region of the material, can be applied to metal soaps only with the assistance of melting aids so as to reduce thermal or oxidative deterimental effects to a tolerable level. Furthermore, these processes use binding agents which adds considerable equipment costs as well as the attendant disadvantage discussed above. If this process could be used without binding agents, if such were possible, a compacted granulate would result. The reason why these processes never attained commercial importance can be found in the unsatisfactory dispersability and reactivity of the dense metal soaps thus obtained.

The object of the present invention is the preparation of a pure metal soap granulate, or mixtures thereof, in which the production is accomplished in a combined operation to eliminate high energy costs and without the use of binding agents or melting aids, resulting in a product of high reactivity and good dispersability.

SUMMARY OF THE INVENTION

This invention pertains to a method for the manufacture of metal soap granulates by means of reacting at least one aqueous solution or suspension of a metal oxide, metal hydroxide, metal carbonate, basic metal carbonate or mixtures thereof with at least one water insoluble fatty acid of chain length $C_8$ to $C_{32}$, preferably $C_{10}$ to $C_{22}$, having a melting point of over 0° C. and below 100° C. whereby in a combined reaction and granulate forming step the metal compound is reacted with the fatty acid under constant agitation to the point where on the surface of the fatty acid particles a structurally stable crust of metal soap has formed, and whereby subsequently the reaction is carried to completion at temperatures above the melting point of the fatty acid for the formation of a metal salt granulate. The metal soap granulate is especially useful as an additive for thermoplastic materials.

BRIEF DESCRIPTION OF THE DRAWING

FIG. 1 is a photo-micrograph showing the metal soap granulates of Example 31 at a 30–50X magnification.

DESCRIPTION OF THE PREFERRED EMBODIMENTS

The objective of the present invention has been attained by means of a combined reaction and granulate forming process in which the metal oxide, metal hydroxide or metal carbonate, including basic metal carbonate or mixtures thereof is reacted with the fatty acid below its melting point and, if required, in the presence of an acid solvating aid, while being constantly agitated until a structurally stable crust of metal soap has formed on the surface of the fatty acid particles, and completing the reaction at temperatures above the melting point of the fatty acid for the formation of a metal soap granulate. The metal soap granulate thus obtained is isolated and dried by conventional means.

The formation of the stable crust is usually accomplished during the time span of heating the charge from room temperature to the melting point temperature of the fatty acid. The granulate obtained according to the present invention is characteristically composed of hollow spheres or fragments thereof with more or less pronounced efflorescence. The hollow granulate usually has a larger diameter than that of the fatty acid particles. This permits the use of a fatty acid in powder form for the production of metal soaps in the granulated state. The reaction components are usually combined in their stoichiometric ratios. To increase the speed of the reaction, however, it is advantageous to add an excess up to 10% of the metal oxide, metal hydroxide, metal carbonate or basic metal carbonate after the melting point of the fatty acid has been exceeded. The fatty acid/water ratio may be varied over a wide range; useful ratios are from 1:1 to 1:100, preferably, between 1:3 and 1:50 and, most preferably, between 1:4 and 1:20. At high acid concentrations intensive or vigorous stirring and mixing is usually required to prevent caking of the granulate.

The first phase of the reaction is accomplished as soon as a structurally stable crust of metal soap has formed on the surface of the fatty acid particles. This is evidenced by the fact that the crust becomes so strong during reaction below the melting point that completion of the reaction at temperatures above the melting point of the fatty acid does not decompose the crust into finely dispersed metal soap particles.

Metal soaps of lithium, magnesium, calcium, strontium, barium, lead, zinc and cadmium in granulated form constitute the embodiment of this invention. For their manufacture, the oxides, hydroxides, carbonates, basic carbonates and mixtures thereof of lithium, magnesium calcium, strontium, barium, lead, zinc and cadmium are found to be especially useful. If necessary, the reaction may be carried out in the presence of an acid solvating aid, as with the use of PbO and CdO, for instance. Such acid solvating aids may comprise short chain carboxylic acids, namely formic acid or propionic acid, or mineral acids, such as nitric acid. The use of an acid solvating aid is desirable if the reaction components coagulate above the melting point temperature of the fatty acid. As disclosed in the German Auslegeschrift 11 89 873 the oxides and hydroxides of magnesium and zinc, which normally are not capable of a direct reaction with fatty acids, can be so converted after treatment of their aqueous suspensions with carbon dioxide and the use of the previously mentioned acid solvating aids. All metal compounds may be used either in solid form or, preferably, in the form of aqueous suspensions or solutions. The sequence of combining metal compounds and fatty acid below the melting point of the fatty acid is of no importance.

According to the invention the production of granulated metal soaps may be carried out with aliphatic, saturated, unsaturated, straight chain or branched fatty acids, either natural or synthetic or mixtures of such fatty acids having 8-32 carbon atoms, preferably 10-22 carbon atoms, and having a melting point of above 0° C. and below 100° C. Such useful acids comprise capric, lauric, myristic, palmitic, stearic, arachidic and behenic acid. In addition, wax acid, unsaturated fatty acid, such as erucic acid, as well as hardened and non-hardened commercial fatty acids which may be derived, for example, from tallow, fish oil, sperm oil, coconut oil, palm oil, palm kernel oil, coco palm kernel oil, peanut oil, cottonseed oil, sunflower seed oil, soybean oil, linseed oil, rapeseed oil and stearine are also useful. Furthermore synthetic fatty acids, such as those derived from paraffin oxidation processes may also be used. The fatty acids used may be in the form of powders, beads, flakes or floculated, as well as, extruded or granulated by other means as, for instance, obtained by cooling of an aqueous fatty acid emulsion below the melting point of that acid, Granulation may also take place by spraying a molten fatty acid or emulsified fatty acid into cold water. The particle size of the fatty acid is generally found to be in the range of 10 to $10^4\mu$, preferably between 50 to $5000\mu$, depending somewhat upon the requirements placed on the particle size of the metal soap granulates.

The present invention eliminates the normally required production steps for the isolation of the metal soap, such as the removal of water, washing of the filter cake and comminuting of the dried material, since only the precipitation of the granulate, its isolation and drying is required; the latter being preferably carried out in a tray-drier. The isolation of the granulate is accomplished by means of screening or filtration. The water content of the filtered granulate is not higher than that of a conventional metal soap, precipitated and recovered in a filter press. While metal soaps containing granulating aids tend to cake in the drying process, the granulates produced according to the present invention retain their flow characteristics throughout all phases of production.

If desired, the process of the present invention permits additions to the granulate of predominantly water insoluble additives, such as antioxidants, flame retardants, pigments, stabilizers, co-stabilizers and lubricants. This is best done by adding the materials to the molten fatty acid and to proceed thereafter with the actual production of the metal soap granulates. The present invention thus permits for the very first time the production of all the essential metal soaps used in the plastics industry in pure, dust-free granulated form without the use of granulating aids or expenditure of energy inherently required in the melting and sinter-granulating processes. Economic advantages and the simplicity of the process further enhance the value of this invention. Good reactivity and dispersability provided by the hollow-sphered structure of the metal soap granulates constitute another inventive feature of the process, carrying with it yet the added advantage of exceptionally good flow characteristics.

The following examples demonstrate the various embodiments of the invention. Abbreviations are used in these examples and are defined as follows:
AN=acid number
IN=iodine number
SN=saponification number.

EXAMPLE 1

Calcuim Caprate 34.4 of capric acid (AN 326, titer 31° C.) are emulsified in 200 ml water of 35° C. by mechanical means to a particle size of 0.2-0.3 mm. Then 400 ml of cold water are slowly added with agitation for cooling to 25° C. whereby a fatty acid granulate in suspended form is obtained. After dispersion of 7.6 g calcuim hydroxide (97% active) in this suspension, the mass is stirred first for 30 minutes at 25° C., followed by 30 minutes agitation at 60° C. The hollow-sphered granulate formed is separated in a Buchner funnel and dried. The content of free fatty acid amounts to 0.5%, while a product with only 0.25% of free fatty acid results if stirring at 60° C. is continued for 90 minutes.

EXAMPLE 2

Cadmium Laurate 40.4 g of lauric acid in flake form (AN 278, titer 43°–44° C. and 32.1 g of a filter-moist cadmium hydroxide with a cadmium content of 35% are suspended in 800 ml water of room temperature, followed by stirring for 30 minutes at 35° C. and another 30 minutes at 70° temperature. The resulting granulate composed of fragmented hollow spheres is filtered and dried. The content of free fatty acid of this product is 1.4%. A granulate with only 0.8% free fatty acid is obtained by stirring for 90 minutes at 70° C. temperature.

EXAMPLE 3

Strontium myristate 100 of myristic acid which has been granulated from an aqueous emulsion as described in Example 1 (AN 246, titer 53° C. particle size 0.2–0.3 mm.) and 60.2 g strontium hydroxide octahydrate (97% active) are suspended in one liter of water at 50° C. temperature and stirred for 30 minutes at 50° C. followed by 60 minutes of agitation at 70° C. The hollow formed granulate is filtered and dried. The content of free fatty acid amounts to 1.7%.

EXAMPLE 4

Magnesium palmitate 25 g of powdered palmitic acid (AN 223, titer 60° C., particle size >40μ) and 2.1 g of 96% active magnesium oxide (precipitated, density 70 g/liter, IN 62) are suspended in 500 ml of water at room temperature. This is followed with stirring for 30 minutes at 55° C. and 2 hours at 70° C. The hollow-sphered granulate formed is filtered and dried. The free fatty acid content amounts to 1.3% but if agitation is carried out for 60 minutes only, the granulate still contains 3% of free fatty acid.

EXAMPLE 5

Lithium stearate

A suspension prepared from 55.0 g of granulated stearic acid (An 198, titer 66° C., particle size 100–300μ) and 8.1 g lithium hydroxide monohydrate in 550 ml of water is heated to 80° C. within 10–15 minutes. The remaining free fatty acid at this point is only 12.1%. Stirring is continued at 80° C. for the duration of one more hour and the resultant hollow granulate, which now contains only 0.4% free fatty acid, is filtered and dried.

EXAMPLE 6

Zinc behenate

A suspension consisting of 8.5 g zinc oxide (95% active, precipitated, particle size 50μ, density 5.4 g/cm$^3$) and 67.8 g behenic acid (AN 165, titer 75° C., particle size 0.2–0.3 mm.) which has been obtained as a granulate from an aqueous dispersion as described in Example 1 and is contained in 1.3 liters of water, is stirred first for 30 minutes at 60° C. and then heated to 100° C. After agitation for one hour at this temperature the granulate still contains 4.4% free fatty acid. After 2 hours this is reduced to 2.7% and after 3 hours only 2.0% free fatty acid remains.

EXAMPLE 7

Barium Behenate

To 100 ml of water at 60° C. temperature 23.3 g of barium hydroxide octahydrate is added and into this suspension 50.0 g of behenic acid in flakes form (AN 165, titer 75° C.) is incorporated so that a paste is obtained having an acid/water ratio of 1:2. This paste is then reacted for 15 minutes at 60° C. followed by 15 minutes at 80° C. temperature. When the melting point of the fatty acid is exceeded, momentary viscosity increase takes place requiring vigorous mixing of the mass. The remaining water which has now a pH of 7 is decanted and the resultant granulate consisting of fractured hollow spheres is dried. The free fatty acid content of the end product is 1.3%.

EXAMPLE 8

Calcium Salt of Erucic Acid 34.0 g of erucic acid (AN 165, titer 28°–30° C., IN 73) are emulsified in 300 ml of water at a temperature of 35° C. to a particle size of 0.2–0.3 mm. With continuing agitation 380 ml of cold water are added to cool to 20° C. Then 3.8 g of calcium hydroxide (97% active) is added to the fatty acid suspension and agitation at 20° C. is continued for 30 minutes, followed by heating to 70° C. After reaction for 90 minutes at 70° C., the content of fatty acid is reduced to below 5%. The resulting hollow granulate is isolated and dried.

EXAMPLE 9

Calcium Salt of Hydrogenated Tallow Fatty Acid

A suspension of 7.6 g calcium hydroxide (97% active) in 225 ml of water at room temperature is heated to 55° C. and then 55.8 g of hydrogenated tallow fatty acid in bead form (AN 201, titer 58°–60° C., particle size 200–500μ) is added. The acid/water ratio is 1:4 and the mixture is maintained for 5 minutes at 55° C. The reaction is carried to completion at 80° C. with vigorous agitation. After 30 minutes the content of free fatty acid is reduced to below 1.5% and the granulate formed is filtered and dried.

EXAMPLE 10

Parallel-Experiment

Calcium Salt of Hydrogenated Tallow Fatty Acid 1000 kg of hydrogenated tallow fatty acid are introduced into 10 cubic meter of water at 65° C. temperature with low speed stirring by a gate-type agitator to produce an emulsion of droplet formed particles measuring 0.5–1.0 cm. The charge is cooled to below the melting point of the fatty acid by the slow introduction of cold water at a flow rate of 350 liter per minute. 279.1 g of the thus obtained ball-formed hydrogenated tallow fatty acid (AN 201, titer 58°–60° C., particle size 0.5–1.0 cm diamater) are suspended in 5.5 liter of water together with 38.2 g calcium hydroxide (97% active) resulting in an acid/water ratio of 1:20. To demonstrate the reaction speed below the melting point of the fatty acid, the charge is agitated for 5 hours at a temperature of 55° C. (for the formation of a structurally stable crust, 5–10 minutes of reaction time would have been sufficient). The content of free fatty acid after 1 hour is determined to be 52.3%, after 3 hours 45.1% and, finally, after 5 hours 45.0%. The temperature is now raised to 70° C. and agitation is continued for additional 90 minutes. Thereby the free fatty acid content is reduced to 7.4% within 30 minutes, to 1.1% in 60 minutes and finally to only 0.7% in 90 minutes. The resultant granulate composed of hollow spheres and fragments thereof is isolated and dried.

EXAMPLE 11

Calcium Salt of Hydrogenated Tallow Fatty Acid 3.8 g of calcium hydroxide (97% active) and 27.9 g of hydrogenated tallow fatty acid in bead form (AN 201, titer 58°–60° C., particle size 200–500μ) are emulsified in 1.4 liter of water at room temperature (Acid/water ratio 1:50). The mass is stirred for 30 minutes at 55° C. and finally for 60 minutes at 70° C. The resulting hollow-sphered granulate, having a free fatty acid content of 0.7%, is isolated and dried.

EXAMPLE 12

Ca/Zn Mixed Soap of Hydrogenated Tallow Fatty Acid

A suspension is formed from:
1.0 g calcium hydroxide (97% active)
1.1 g zinc oxide, 95% active, precipitated, highly dispersable, particle size 50μ density 5.4 g/cc and
14.5 g hydrogenated tallow fatty acid in bead form (AN 201, titer 58°–60° C., particle size 200–500μ) contained in 1.4 liter of water at room temperature. (Acid/water ratio 1:100). The charge is agitated for 30 minutes at a temperature of 50° C., followed by 60 minutes agitation at 70° C. The resulting granulate is isolated and dried. Its free fatty acid content is determined as 1.1%.

EXAMPLE 13

Magnesium Salt of Triple Refined Stearine

A suspension is formed from 49.8 g triple refined stearine which has been emulsified in an aqueous system as described in example No. 1 (AN 209, titer 54°–55° C., particle size 0.2–0.3 mm) and 3.9 g of 96% active magnesium oxide (precipitated, bulk density 70 g/ltr. iodine number 62) and 500 ml. of water at 50° C. The temperature of 50° C. is maintained for 10 minutes and then raised to 70° C. for a duration of 2 hours at continuing agitation. The resulting hollow sphered granulate is filtered and dried; its free fatty acid content is less than 2%.

EXAMPLE 14

Barium Salt of Commercial Grade Stearine

A suspension prepared from 27.5 g stearine in bead form (AN 204, titer 56°–58° C., particle size 100–700μ) and 15.8 g of barium hydroxide-octahydrate contained in 600 ml of water at room temperature is heated within 15 minutes to 50° C. and maintained at this temperature for 5 minutes. Then the temperature is raised to 70° C. and the charge is stirred for 30 minutes. The resulting hollow granulate containing 0.25% free fatty acid is filtered and dried.

EXAMPLE 15

Barium Salt of Fatty Acid, derived from Coconut Oil 49.5 g of the fatty acid (AN 272, titer 23°–25° C., IN 8) are suspended in 500 ml of water at a temperature of 30° C. which is transformed into a gel-like mass by slow cooling to 18° C. Upon introduction of 38.0 g of barium hydroxide octahydrate the mass is transformed to a powdery state. First the suspension is stirred for 30 minutes at 20° C., followed by 60 minutes of agitation at 70° C. The resulting granulate, which contains 2.4% free fatty acid, is filtered and dried.

EXAMPLE 16

Calcium Salt of Hydrogenated Fatty Acid derived from Palmkernel Oil 22.5 g of hydrogenated fatty acid in sliced form (AN 249, titer 33° C.) are mechanically emulsified in 450 ml water at 40° C. to a particle size of 0.2–0.3 mm. Through slow cooling to 25° C. with agitation, the fatty acid is granulated. After addition of 3.8 g calcium hydroxide (97% active), the suspension is stirred for 30 minutes at 25° C., followed by 15 minutes of agitation at 70° C. The hollow-sphered granulate obtained is isolated and dried. The content of free fatty acid amounts to 3%.

EXAMPLE 17

Calcium Salt of Hydrogenated Fatty Acid derived from Fish Oil 27.9 g of hydrogenated fatty acid, emulsified as described in Example 1 (AN 201, titer 51°–52° C., IN 4, particle size 0.2–0.3 mm) and 3.8 g calcium hydroxide (97% active) are suspended in 550 ml water at 48° C. temperature. The mass is stirred for 30 minutes at this temperature, followed by agitation at 70° C. for the duration of one hour. A hollow-sphered granulate, with a free fatty acid content of 2.5% is isolated and dried.

EXAMPLE 18

Calcium Salt of non-hardened Tallow Fatty Acid 81.3 g of tallow fatty acid (AN 207, titer 46° C., IN 41) are emulsified by mechanical means in 800 ml of water at 55° C. to a particle size of 0.2–0.3 mm. and then granulated by the addition of 800–1000 ml of cold water. After addition of 11.5 g of calcium hydroxide (97% active) the charge is agitated for 30 minutes at a temperature of 35° C. followed by one hour at about 100° C. with a reflux condenser. Under these operating conditions a granulate with less than 5% free fatty acid is obtained. The reaction can be accelerated if a small excess of calcium hydroxide is added. It is advantageous to add this excess calcium hydroxide after the free fatty acid has been reduced to about 10%. In the presence of an excess of 1.1 g calcium hydroxide a granulate is thus obtained which, after reaction for two hours at 100° C., contains only 1.0% free fatty acid. The resulting hollow-sphered granulate is isolated and dried.

EXAMPLE 19

Calcium Salt of Montan Wax Fatty Acid 45.0 g of fatty acid (AN 125, drop point 84° C.) are emulsified by mechanical means in 500 ml water at 90° C. to a particle size of 0.2–0.3 mm. By slow cooling to 60° C. a suspension of granulated fatty acid is obtained. To this suspension 3.8 g of calcium hydroxide (97% active) is added and the mass is stirred at 60° C. for 50 minutes. The reaction is carried to completion at 90° C. After 30 minutes 2% free fatty acid is found, while after an additional 60 minutes of reaction time only 1.1% free fatty acid is present. The resulting hollow-sphered granulate is filtered and dried.

EXAMPLE 20

Calcium Salt of a Synthetic Fatty Acid derived by Paraffin Oxidation 76.5 g of synthetic fatty acid derived by paraffin oxidation (AN 197, SN 220, IN 14, titer 50° C., predominantly straight chained) are emulsified by mechanical means in 500 ml of water at 60° C. to a particle size of 0.2–0.3 mm. With agitation, an additional 1000 ml of cold water are used for cooling to 35° C. After introduction of 11.5 g of calcium hydroxide (97% active), the temperature is maintained at 30° C. for 30 minutes (pH 11), followed by boiling at reflux for 30 minutes (pH 7). The granulate obtained is separated on a Buchner funnel and dried, its content of free fatty acid amounts to 0.8%.

EXAMPLE 21

Zinc Salt of Hydrogenated Fatty Acid obtained from Rapeseed Oil

Using low speed agitation an emulsion is prepared from 62.2 g fatty acid (AN 180, titer 62°–64° C.) in 300 ml water at 80° C. temperature, to be transformed into granular form of fatty acid by the careful addition of 320 ml water at a temperature of 10° C. After introduction of a concentrated suspension of 8.6 g zinc oxide (95% active, highly dispersable, precipitated, particle size 50$\mu$, density 5.4 g/cc) the mass is stirred for 30 minutes at 60° C. temperature, followed by 90 minutes at 90° C. The resulting hollow-sphered granulate with a free fatty acid content of 2.8% is filtered and dried.

EXAMPLE 22

Zinc Salt of Hydrogenated Tallow Fatty Acid 27.9 g of hydrogenated tallow fatty acid in bead form (AN 201, titer 58°–60° C., particle size 200–500$\mu$) and 35.1 g of filtermoist zinc hydroxide (9.4% zinc content) are suspended in 550 ml of water. The zinc hydroxide has been prepared by precipitation with sodium hydroxide of an aqueous zinc sulfate solution, and washed free from soluble zinc salts. The slurry is stirred first for 30 minutes at room temperature followed by one hour at 62° C. The resulting hollow granulate is filtered and dried. Free fatty acid content of 0.8%; ash 13.4% and melting point of 120° C. are determined.

EXAMPLE 23

Zinc Salt of Hydrogenated Tallow Fatty Acid 27.9 g of fatty acid in bead form (AN 201, titer 58°–60° C., particle size 200–500$\mu$) and 5.65 g of a commercial grade basic zinc carbonate (zinc content 57.9%) are suspended in 550 ml of water at room temperature. The mass is stirred for 60 minutes at 50° C. followed by 2 hours at 70° C. The hollow-sphered granulate obtained, having a free acid content of 0.8%, ash 13.5% and melting point of 120° C., is isolated and dried. A similar good result is obtained if the suspension is prepared at 55° C. and is stirred for only 10 minutes at this temperature before the reaction is carried to completion at 70° C. as described above.

EXAMPLE 24

Zinc Salt of Hydrogenated Tallow Fatty Acid

A suspension is prepared from:
83.6 g hydrogenated tallow fatty acid in bead form (AN 201, titer 58°–60° C., particle size 200–500$\mu$)
12.8 g zinc oxide, produced by the American method in a rotary oven, particle size 1.5$\mu$ max., density 5.7 g/cc, 99% active) and
1.5 liter of water.

According to German Auslegeschrift 11 89 973 carbon dioxide is injected at a slow rate into this suspension over a period of 3 hours. After addition of 3.0 ml acetic acid (60% active) the charge is stirred first for 30 minutes at 50° C. followed by agitation at 70° C. for one hour. The resulting hollow-sphered granulate which contains 1.4% free fatty acid, ash content 13.5% and has a melting point of 120° C. is isolated and dried.

EXAMPLE 25

Cadmium Salt of Hydrogenated Tallow Fatty Acid 27.9 g of fatty acid in bead form (AN 201, titer 58°–60° C., particle size 200–500$\mu$) and 6.4 cadmium oxide are suspended in 550 ml of water at 55° C. temperature to which 0.5 ml of acetic acid (60% active) is added. The mass is stirred for 10 minutes at 55° C., followed by heating to 80° C. After stirring for 60–70 minutes the charge takes on a white color. Agitation is continued for an additional 30 minutes before the granulate is finally filtered and dried. The content of free fatty acid is 0.7%.

EXAMPLE 26

Lead Salt of Commercial Grade Stearene 27.5 g of a commercial grade stearine in bead form (AN 204, titer 56°–58° C., particle size 100–700$\mu$) and 14.0 g of filter-moist lead hydroxide (lead content 74%) are suspended in 550 ml water of room temperature. The charge is stirred 30 minutes at 55° C. followed by 15 minutes of agitation at 70° C. The hollow-sphered granulate containing 1.6% free fatty acid is filtered and dried.

EXAMPLE 27

Lead Salt of Hydrogenated Tallow Fatty Acid 11.2 g of lead oxide and 27.9 g of hydrogenated tallow fatty acid (AN 201, titer 58°–60° C., particle size 200–500$\mu$) are suspended in 550 ml of water at room temperature.

After addition of 0.5 ml of 60% acetic acid the charge is stirred for 30 minutes at 50° C., followed by 15 minutes agitation at 70° C. The hollow-sphered granulate formed is filtered and dried. The fatty acid content is 1.5%. Equally good results are obtained also if the suspension if prepared at 55° C. and maintained at this temperature for 5 minutes only, before the reaction is continued above the melting point of the fatty acid, as has been described above. The free fatty acid content is 1.9% in this instance.

EXAMPLE 28

Lead Salt of Commercial Grade Stearine

To a suspension prepared from 27.9 g of fatty acid in bead form (AN 201, titer 58°–60° C., particle size 200–500$\mu$) and 11.2 g lead oxide contained in 550 ml of water, 0.5 g of concentrated nitric acid is added. The charge is stirred first for 30 minutes at 50° C., followed by heating to 70° C. The nearly colorless granulate contains 3.3% free fatty acid after reaction for only 15 minutes, but after 60 minutes of agitation only 2.0% of free fatty acid remains. The resulting hollow-sphered granulate is filtered and dried.

EXAMPLE 29

Barium Salt of Hydrogenated Tallow Fatty Acid

A mixture consisting of 38.2 g fatty acid (AN 201, titer 58°-60° C.) and 2.5 g of 2,6-di-tert-butyl-4-hydroxytoluol is melted and then emulsified in hot water to a particle size of 0.2-0.3 mm. with granulation following by means of slow cooling to 55° C. After addition of 21.6 g barium hydroxide octahydrate, the charge is stirred for 30 minutes at 55° C. followed by agitation at 70° C. for one hour. The resulting hollow-sphered granulate, containing 1.5% free fatty acid is filtered and dried.

EXAMPLE 30

Calcium Salt of Hydrogenated Tallow Fatty Acid

A reaction vessel equipped with an agitator and heating mantel is charged with 137 kg of lime (Calcium hydroxide content 97%). After heating to 50° C., 1000 kg of hydrogenated tallow fatty acid in bead form (AN 201, titer 58°-60° C., particle size 200-500$\mu$) are added within a period of 15 minutes and the charge is stirred for 30 minutes at 50° temperature. This is followed by heating to 70° C. with agitation for 30 minutes at that temperature. The resulting hollow-sphered granulate is separated over a fine-mesh screen and dried in a forced draft oven with exit temperature of 70°-75° C. Analysis of the product shows 0.3% free fatty acid, 0.9% ash, 1.5% moisture content and melting point 155°-160° C.

EXAMPLE 31

Calcium Salt of Commercial Stearine 27.5 g of stearic acid in bead form (AN 204, titer 56°-59° C., particle size 1.5 m/m) and 3.7 g lime are suspended in 600 ml of cold water and then heated within 10-15 minutes to 70° C. while the charge is vigorously agitated. After 30 minutes of continuing agitation the hollow-sphered granulate formed is isolated and dried. The photo-micrograph (magnification 30-50 X) of FIG. 1 depicts three particle sizes in the range of 1.0-1.5 mm of the granulate obtained. The invention feature of the hollow-sphered configuration is shown clearly in the photo-micrograph.

We claim:

1. A process for the preparation of metal soap granulates or mixtures thereof which comprises:
    (a) reacting an aqueous solution or suspension of a metal compound selected from metal oxide, metal hydroxide, metal carbonate, basic metal carbonate or mixtures thereof with a water insoluble $C_8$ to $C_{32}$ fatty acid or mixtures thereof having a melting point above 0° C. and below 100° C., said reaction conducted at a temperature below the melting point of said fatty acid or mixtures thereof, in the absence of catalysts or wetting agents, and under constant agitation until a structurally stable metal soap crust forms on the surface of the fatty acid
    (b) continuing the reaction to completion at a temperature above the melting point of said fatty acid or mixtures thereof whereby metal soap granulates are formed as a product.

2. A process according to claim 1 wherein stoichiometric quantities of the metal compound and the fatty acid are reacted.

3. A process according to claim 1 wherein a stoichiometric excess of metal compound is added to the reaction mixture after the temperature of the mixture is above the melting point of the fatty acid.

4. A process according to claim 1 wherein step (a) is conducted in the presence of an acid solvating aid.

5. A process according to claim 1 wherein the weight ratio of fatty acid to water is from 1:1 to 1:100.

6. A process according to claim 1 wherein the weight ratio of fatty acid to water is from 1:3 to 1:50.

7. A process according to claim 1 wherein the weight ratio of fatty acid to water is from 1:4 to 1:20.

8. A process according to claims 5, 6 and 7 wherein with high acid concentrations vigorous mixing is employed.

9. A process according to claim 1 wherein the fatty acid is in the form of powder, beads, flakes, extrusions or granulates.

10. A process according to claim 1 wherein the particle size of the fatty acid is in the range of 10 to $10^4\mu$.

11. A process according to claim 1 wherein the particle size of the fatty acid in the range of 50 to 5000$\mu$.

12. A process according to claim 1 wherein the metal is lithium, magnesium, calcium, strontium, barium, lead, zinc or cadmium.

13. A process according to claim 4 wherein the metal compound is the oxide or hydroxide of magnesium or zinc and said compound is treated with $CO_2$ prior to its reaction with the fatty acid.

14. A process according to claim 13 wherein the acidic solvating aid is a short chain carboxylic acid or a mineral acid.

15. A process according to claim 13 wherein the acidic solvating aid is formic, acetic, propionic or nitric acid.

16. A process according to claim 1 wherein the fatty acid is capric, lauric, myristic, palmitic, stearic, arachidic, behenic, wax or erucic acid or is derived from tallow, fish oil, sperm oil, coconut oil, palm oil, palm kernel oil, coco palm kernel oil, peanut oil, cottonseed oil, sunflower seed oil, soybean oil, linseed oil, rapeseed oil or stearine or synthetic fatty acids from paraffin oxidation.

17. A process according to claim 1 or 16 wherein the fatty acid is a $C_{10}$ to $C_{22}$ fatty acid or mixtures thereof.

18. A process according to claim 1 including the following additional step:
    adding predominantly water insoluble antioxidants.

19. A metal soap granulate prepared by the process of claims 1, 2, 3, 4, 5, 6, 7, 9, 10, 11, 12, 13, 14, 15, 16 or 18.

20. The process of claim 18 wherein the additional step is adding flame retardants.

21. The process of claim 18 wherein the additional step is adding pigments.

22. The process of claim 18 wherein the additional step is adding stabilizers or costabilizers.

23. The process of claim 18 wherein the additional step is adding lubricants.

* * * * *